(12) United States Patent
Loebl et al.

(10) Patent No.: US 10,299,935 B2
(45) Date of Patent: May 28, 2019

(54) ADJUSTABLE ARCUATE IMPLANT

(71) Applicant: SEASPINE, INC., Carlsbad, CA (US)

(72) Inventors: Oded Loebl, Tel Mond (IL); Didier Toubia, Raanana (IL)

(73) Assignee: SeaSpine, Inc., Carlsbad, CA (US)

( * ) Notice: Subject to any disclaimer, the term of this patent is extended or adjusted under 35 U.S.C. 154(b) by 99 days.

(21) Appl. No.: 15/125,164

(22) PCT Filed: Mar. 12, 2015

(86) PCT No.: PCT/IB2015/051820
§ 371 (c)(1),
(2) Date: Sep. 11, 2016

(87) PCT Pub. No.: WO2015/136484
PCT Pub. Date: Sep. 17, 2015

(65) Prior Publication Data
US 2017/0172760 A1    Jun. 22, 2017

Related U.S. Application Data

(60) Provisional application No. 61/951,589, filed on Mar. 12, 2014.

(51) Int. Cl.
*A61F 2/44* (2006.01)
*A61F 2/46* (2006.01)
*A61F 2/30* (2006.01)

(52) U.S. Cl.
CPC .......... *A61F 2/4465* (2013.01); *A61F 2/4455* (2013.01); *A61F 2/4611* (2013.01);
(Continued)

(58) Field of Classification Search
CPC ........ A61F 2/44; A61F 2/4465; A61F 2/4455; A61F 2/46; A61F 2/4611
See application file for complete search history.

(56) References Cited

U.S. PATENT DOCUMENTS

2004/0162618 A1   8/2004  Mujwid et al.
2005/0125062 A1*  6/2005  Biedermann ........... A61F 2/442
                                                 623/17.11
(Continued)

OTHER PUBLICATIONS

European Patent Office, International Search Report and Written Opinion for App. No. PCT/IB2015/051820 dated Jun. 5, 2015, 12 pages.

*Primary Examiner* — Christopher Beccia
(74) *Attorney, Agent, or Firm* — Middleton Reutlinger; Robert H. Eichenberger; Chad D. Bruggeman (57) ABSTRACT

An expanding implant (10, 10', 10") includes a base (12) having a contact surface (14) for contacting a first region of tissue and a displaceable portion. (24) having a contact surface (26) for contacting a second region of tissue. The base (12) has a proximal portion (16) in sliding engagement with, a distal portion (18) so as to define an arcuate path of relative motion between the proximal and distal portions. The base assumes an initial state with a first arcuate extent and is adjustable towards a second State by changing an: extent of overlap between the proximal and distal portions to vary an. arcuate extent of the base. First and second rigid linking segments (20, 22) are in articulating connection with the distal and proximal portions of the base, and with the displaceable portion such that adjustment of the base from the initial state towards the second state causes an increase in a distance between the contact surfaces of the base and the displaceable portion.

16 Claims, 11 Drawing Sheets

(52) U.S. Cl.
CPC ....... *A61F 2/44* (2013.01); *A61F 2002/30133* (2013.01); *A61F 2002/30308* (2013.01); *A61F 2002/30362* (2013.01); *A61F 2002/30372* (2013.01); *A61F 2002/30398* (2013.01); *A61F 2002/30471* (2013.01); *A61F 2002/30489* (2013.01); *A61F 2002/30556* (2013.01); *A61F 2002/30579* (2013.01); *A61F 2002/30601* (2013.01); *A61F 2002/30649* (2013.01); *A61F 2002/30777* (2013.01); *A61F 2002/30891* (2013.01); *A61F 2002/4475* (2013.01); *A61F 2002/4627* (2013.01); *A61F 2310/00023* (2013.01)

(56) References Cited

U.S. PATENT DOCUMENTS

| | | | |
|---|---|---|---|
| 2005/0209698 A1 | 9/2005 | Gordon | |
| 2013/0041471 A1* | 2/2013 | Siegal | A61F 2/442 623/17.16 |
| 2014/0172103 A1* | 6/2014 | O'Neil | A61F 2/447 623/17.16 |

* cited by examiner

ADJUSTABLE ARCUATE IMPLANT

FIELD AND BACKGROUND OF THE INVENTION

The present invention relates to orthopedic implants and, in particular, it concerns an expanding arcuate implant for insertion between two regions of tissue.

It is known to employ arcuate implants, in certain applications referred to informally as a "banana cage". In the particular example of intervertebral fusion, the curvature of the arcuate implant is typically intended to fit to the curvature of the anterior portion intervertebral space. An example of such an implant may be found in U.S. Pat. No. 7,500,991.

SUMMARY OF THE INVENTION

The present invention is an expanding arcuate implant for insertion between two regions of tissue.

According to the teachings of an embodiment of the present invention there is provided, an expanding implant for insertion between two regions of tissue, the implant comprising: (a) a base having a contact surface for contacting a first region of tissue, the base comprising a proximal portion in sliding engagement with a distal portion so as to define an arcuate path of relative motion between the proximal and distal portions, the base assuming an initial state with a first arcuate extent and being adjustable towards a second state by changing an extent of overlap to vary an arcuate extent of the base; (b) a first rigid linking segment in articulating connection with the distal portion of the base; (c) a second rigid linking segment in articulating connection with the proximal portion of the base; and (d) a displaceable portion having a contact surface for contacting a second region of tissue, the displaceable portion being in articulating connection with the first linking segment and with the second linking segment such that adjustment of the base front the initial state towards the second state causes are increase in a distance between the contact surfaces of the base and the displaceable portion.

According to a further feature of an embodiment of the present invention, the adjustment of the base from the initial state towards the second state corresponds to a shortening of the base by increasing an extent of overlap between the first and second portions.

According to a further feature of an embodiment of the present invention, the articulating connections of the first and second linking segments with each of the proximal portion, the distal portion and the displaceable portion are polyaxial joints.

According to a further feature of an embodiment of the present invention, the articulating connections of the first and second linking segments with each of the proximal portion, the distal portion and the displaceable portion are ball-and-socket joints.

According to a further feature of an embodiment of the present invention, the displaceable portion includes at least one arcuate bearing surface, and wherein the proximal portion and the distal portion of the base each include at least one arcuate abutment surface in sliding engagement with the bearing surface, thereby at least partially defining the arcuate path of relative motion between the proximal portion and the distal portion.

According to a further feature of an embodiment of the present invention, the displaceable portion and the base are each formed with openings through their respective contact surfaces such that the openings provide at least one unobstructed path between the first and second regions of tissue.

According to a further feature of an embodiment of the present invention, the proximal portion and the distal portion of the base are formed with complementary parts of a ratchet configuration configured to allow adjustment of the base towards the second state and to oppose return of the base back towards the initial state.

According to a further feature of an embodiment of the present invention, the ratchet configuration includes a first series of ratchet teeth deployed along an inner side of an arcuate form of the implant and a second series of ratchet teeth deployed along an outer side of the arcuate form of the implant, wherein an inter-tooth spacing of the second series of ratchet teeth is greater than an inter-tooth spacing of the first series of ratchet teeth.

According to a further feature of an embodiment of the present invention, the ratchet configuration includes a plurality of teeth, each of the teeth having a tooth edge, the ratchet configuration being oriented such that the tooth edges are aligned substantially perpendicular to a plane containing the arcuate path of relative motion.

According to a further feature of an embodiment of the present invention, the ratchet configuration includes a plurality of teeth, each of the teeth having a tooth edge, the ratchet configuration being oriented such that the tooth edges are substantially within to a plane containing the arcuate path of relative motion.

According to a further feature of an embodiment of the present invention, there is also provided an elongated holder having a direction of elongation, the expanding implant being pivotally connected to a distal end of the elongated holder so as to be pivotable about a pivot axis between an insertion position in which the distal portion is aligned with the direction of elongation and a laterally deflected position, the pivot axis being perpendicular to the arcuate path of relative motion.

According to a further feature of an embodiment of the present invention, there is also provided a locking element extending along the elongated holder for selectively engaging a corresponding recess in the proximal portion so as to lock the expanding implant in the insertion position, the locking element being selectively retractable so as to release the expanding implant to deflect towards the laterally deflected position.

According to a further feature of an embodiment of the present invention, there is also provided a tensioning element extending along the elongated holder and along the proximal portion, the tensioning element being connected to the distal portion such that tension applied to the tensioning element is effective to shorten the base towards the second state.

There is also provided according to the teachings of an embodiment of the present invention, a method of use of the aforementioned implant and holder, the method comprising the steps of: (a) using the holder to introduce the implant in the insertion state between two vertebral endplates; (b) pivoting the implant to the laterally deflected position and deploying the implant in an anterior half of an intervertebral space; and (c) causing relative motion of the base portions so as to press the contact surfaces against the two vertebral endplates; and (d) detaching the holder from the implant so as to leave the implant as a spacer between the vertebral endplates.

According to a further feature of an embodiment of the present invention, a quantity of bone-promoting material is introduced into an inner volume of the implant as part of an intervertebral fusion process.

BRIEF DESCRIPTION OF THE DRAWINGS

The invention is herein described, by way of example only, with reference to the accompanying drawings, wherein.

DESCRIPTION OF THE PREFERRED EMBODIMENTS

The present invention is an expanding arcuate implant for insertion between two regions of tissue.

The principles and operation of implants and corresponding methods according to the present invention may be better understood with reference to the drawings and the accompanying description.

Referring now to the drawings, FIGS. 1A-10 illustrate an expanding implant, generally designated 10, constructed and operative according to a first embodiment of the present invention, for insertion between two regions of tissue. In general terms, implant 10 has a base 12 with a contact surface 14 for contacting a first region of tissue. Base 12 includes a proximal portion 16 in sliding engagement with a distal portion 18 so as to define an arcuate path of relative motion between proximal and distal portions 16 and 18. Base 12 assumes an initial state (FIGS. 1A, 2A, 3A, 4A and 6A) with a first arcuate extent and being adjustable towards a second state by changing an extent of overlap to vary an arcuate extent of the base (FIGS. 3B and 3C). As best seen in the exploded views of FIGS. 5A and 5B, a first rigid linking segment 20 is in articulating connection with distal portion 18 of the base, and a second rigid linking segment 22 is in articulating connection with proximal portion 16 of the base. A displaceable portion 24, with a contact surface 26 for contacting a second region of tissue, is in articulating connection with first linking segment 20 and with second linking segment 22 such that adjustment of the base from the initial state towards the second state causes an increase in a distance between contact surface 14 of base 12 and contact surface 26 of displaceable portion 24.

In the non-limiting set of particularly preferred implementations illustrated herein, adjustment of base 12 from the initial state towards the second state corresponds to a shortening of the base (i.e., a reduction in the arcuate extent) by increasing an extent of overlap between the first and second portions 16 and 18. In this case, articulating connection of linking segment 20 to distal portion 18 is preferably at a distal region of distal portion 18 while articulating connection of linking segment 22 to proximal portion 16 is preferably at a proximal region of proximal portion 16. It should be noted that reverse implementations in which proximal and distal portions 16 and 18 reduce their extent of overlap and increase the arcuate extent of base 12 during expansion of the implant height also fall within the scope of the present invention.

At this stage, it will already be apparent that the implants of the present invention provide particular advantages. The expansion mechanism employed to adjust the height of the implant is particularly simple and reliable. At the same time, the use of an arcuate path of relative motion between proximal and distal portions 16 and 18 of the base ensures that the preferred arcuate geometry of the implant is maintained over the full range of adjustment.

Figure 1A:
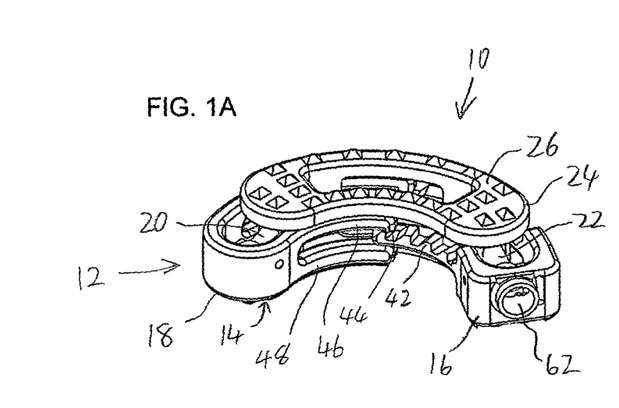
FIGS. 1A and 1B are isometric views of an expanding implant, constructed and operative according to an embodiment of the present invention, shown in a low profile state and an expanded state, respectively.
Figure 1B:
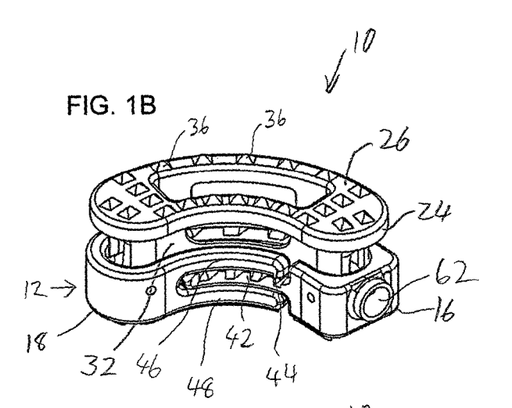
Figure 2A:
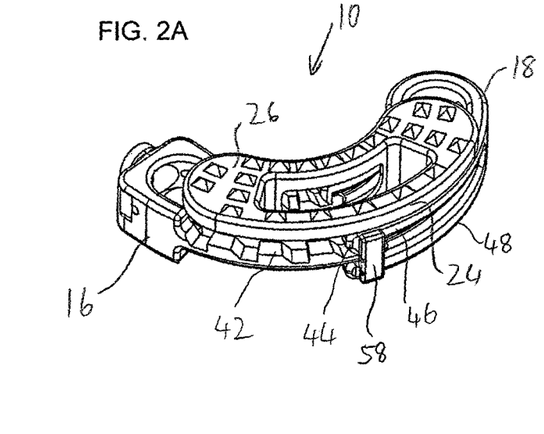
FIGS. 2A and 2B are additional isometric views of the expanding implant of FIG. 1A shown in the low profile state and an expanded state, respectively.
Figure 2B:
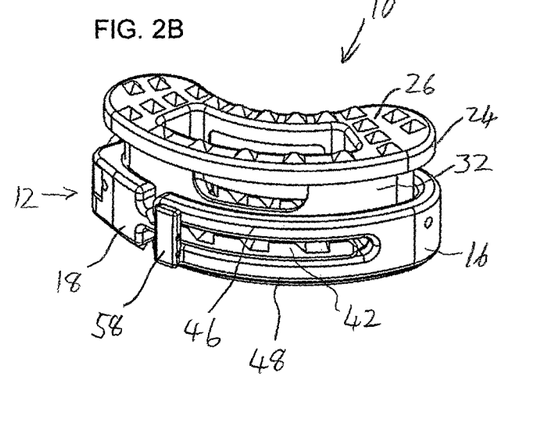
Figure 3A:
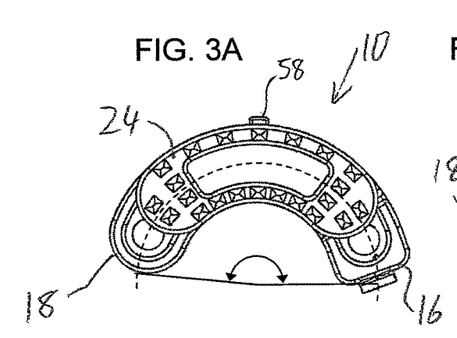
FIGS. 3A-3C are a sequence of plan views of the implant of FIG. 1A in successive stages of deployment from the low profile state to successively more expanded states.
Figure 3B:
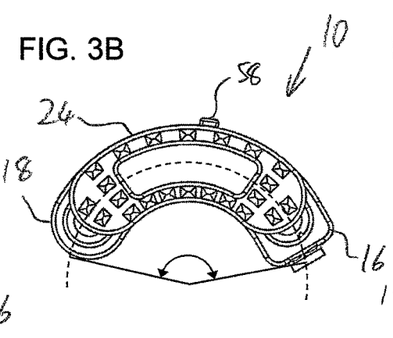
Figure 3C:
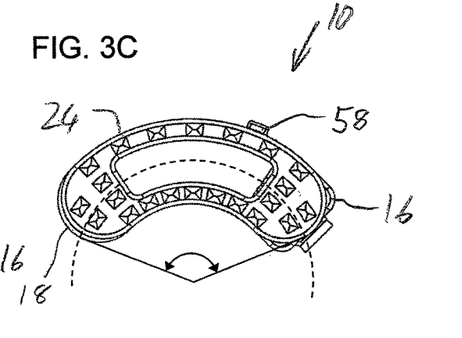
Figure 4A:
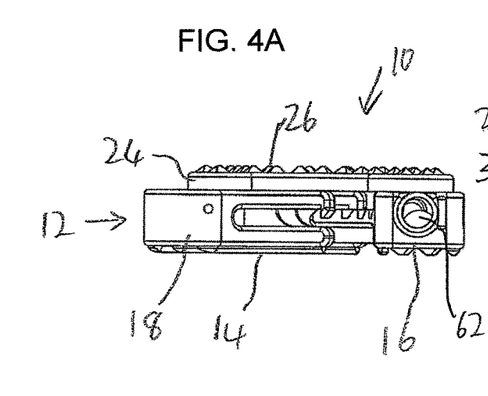
FIGS. 4A-4C are a sequence of side views corresponding to the states of FIGS. 3A-3C, respectively.
Figure 4B:
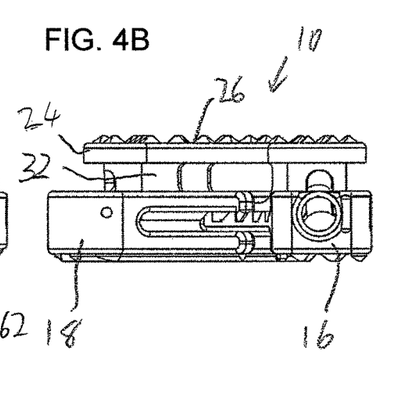
Figure 4C:
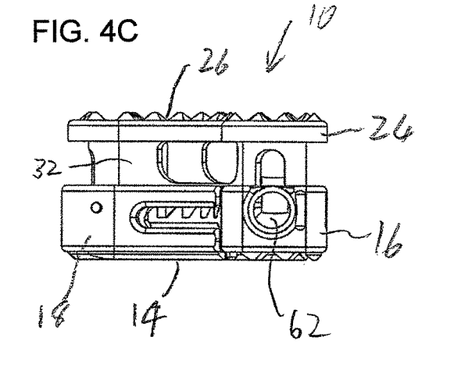
Figure 5A:
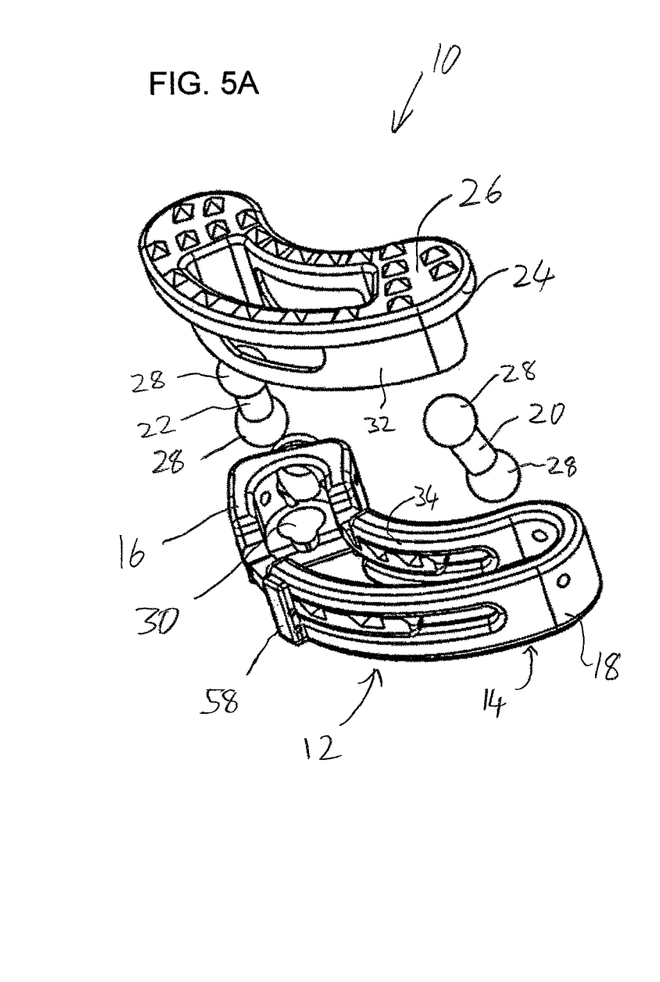
FIGS. 5A and 5B are, respectively, upper and lower isometric exploded views of the implant of FIG. 1A.
Figure 5B:
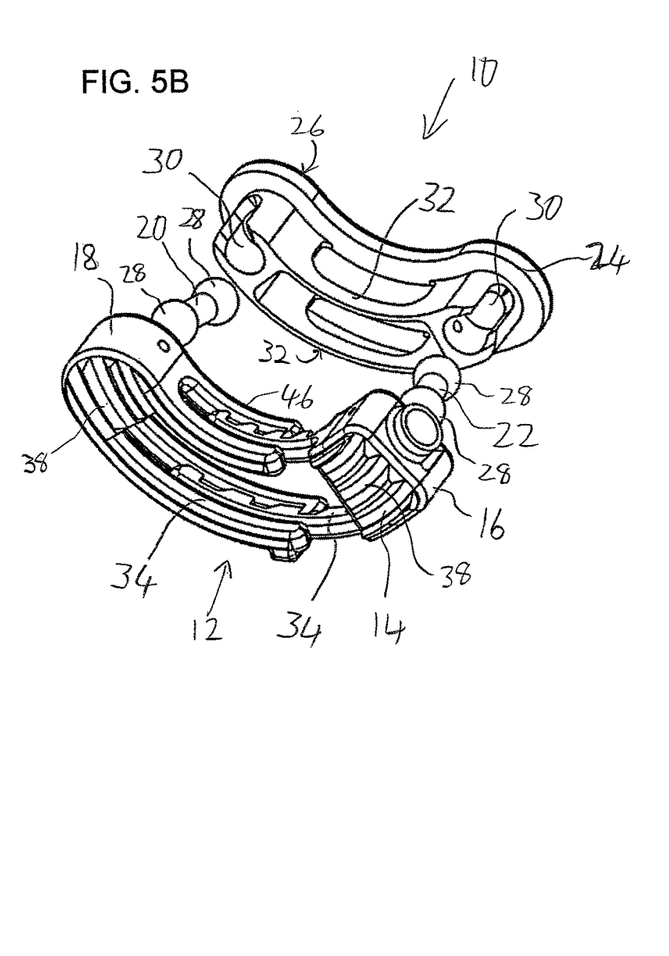
Figures 6A, 6B:
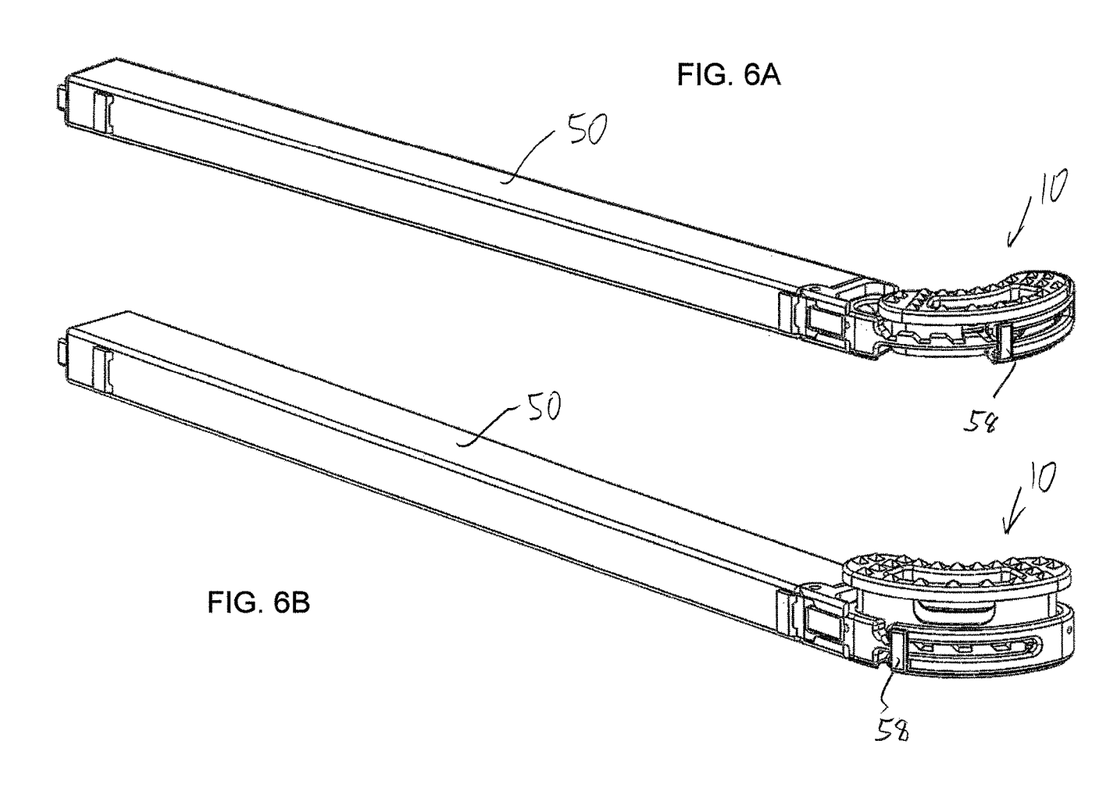
FIGS. 6A and 6B are isometric views of the implant of FIG. 1A attached to an elongated holder, the implant being shown in the low profile state and an expanded state, respectively.

In order to accommodate the varying geometry between the linking segments and the portions of the base as the arcuate extent changes, the articulating connections of first and second linking segments 20 and 22 with proximal portion 16, distal portion 18 and displaceable portion 24 are preferably implemented as polyaxial joints. In the particularly preferred but non-limiting example illustrated here, the articulating connections are implemented as ball-and-socket joints, with a "ball" 28 on both ends of linking segments 20 and 22 which engage complementary "sockets" 30 formed in proximal portion 16, distal portion 18 and displaceable portion 24, all as best seen in FIGS. 5A and 5B. In the implementation illustrated here, the region around sockets 30 in displaceable portion 24 is formed with a guide slot 32 which helps to limit the range of motion of the ball-and-socket joint to the range required during adjustment of the implant. It should be noted that other forms of polyaxial joint, such as for example a pivotal connection with an additional swivel linkage, or an integrally formed flexible joint formed of polymer with suitable degrees of freedom, may also be used.

The use of two linking segments with polyaxial joints does not fully define the orientation of displaceable portion 24 relative to base 12. Accordingly, certain preferred implementations of the present invention employ guide surfaces in sliding engagement to further define the spatial relation between displaceable portion 24 and base 12. Thus, in the example illustrated here, displaceable portion includes at least one, and in this case two, arcuate bearing surfaces 32 which are in sliding engagement with complementary surfaces of at least one of proximal and distal portions 16, 18. In a particularly preferred case, as illustrated herein, both proximal portion 16 and distal portion 18 include at least one arcuate abutment surface, and preferably a pair of such surface 34, for sliding, engagement with bearing surfaces 32, thereby at least partially defining the arcuate path of relative motion between proximal portion 16 and distal portion 18.

One particularly advantageous but non-limiting set of applications of the present invention employ implant 10 as an expanding cage for use in intervertebral fusion procedures. For this purpose, both contact surface 14 and contact surface 26 are typically formed with various protecting features, such as spikes or pyramids 36. For surface 14, due to the arcuate sliding motion that occurs during adjustment of the implant, arcuate ridges 38 (FIG. 5B) may be preferred.

Additionally, displaceable portion 24 and base 12 are each preferably formed with one or more openings 40 through their respective contact surfaces 14 and 26 such that the openings provide at least one unobstructed path between the first and second regions of tissue. This facilitates formation of a continuous bone bridge between the adjacent vertebral bodies, passing through the interior of implant 10.

Implant 10 preferably also includes an arrangement for maintaining a deployed (raised) state of the implant. According to one particularly preferred but non-limiting set of implementations, this is achieved by forming proximal portion 16 and distal portion 18 with complementary parts of a ratchet configuration configured to allow adjustment of the base towards the second state and to oppose return of the base back towards the initial state. In the implementation shown here, proximal portion 16 is formed with arcuate sequences of ratchet teeth 42 which are engaged by a tooth 44 deployed on a resilient arm 46, functioning effectively as a pawl. The ratchet configuration is configured as an arcuate structure to match the arcuate path of relative motion of the proximal and distal portions of the base, and is preferably implemented on both the inside and the outside of the arcuate form. Taking into consideration the differing radii of curvature, the series of ratchet teeth deployed along the outer side preferably have a greater inter-tooth spacing than the series of ratchet teeth deployed along the inner side of the arcuate form so as to provide bilateral locking at the same positions along the arcuate path of motion. A second arcuate arm 48 runs parallel to arm 46 to define a track within which ratchet tooth sequence 42 is engages, thereby also maintaining alignment of the proximal and distal portions 16 and 18.

There are various options for the orientation of the ratchet configuration. These can most clearly be defined by referring to a "tooth edge" of the ratchet teeth, defined as the line of intersection of the main leading ("rise") surface and trailing ("fall") surface of each ratchet tooth, or in the case of a flat-topped tooth, between the flat top and the trailing fall surface.

In the exemplary implementation of FIGS. 1A-10, the ratchet configuration is oriented such that the tooth edges are substantially within a plane containing the arcuate path of relative motion. The corresponding motion of the engaging tooth 44 moving across this ratchet is therefore an up/down motion, i.e., in the direction of expansion of the implant.

Figure 11A:
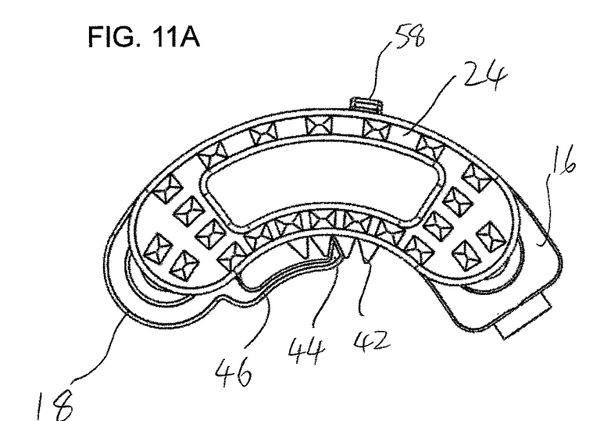
FIGS. 11A-11C are a plan view, an upper isometric view and a low isometric view, respectively, of a first variant implementation of an expanding implant, constructed and operative according to an embodiment of the present invention, employing a first alternative implementation of a ratchet configuration.
Figure 11B:
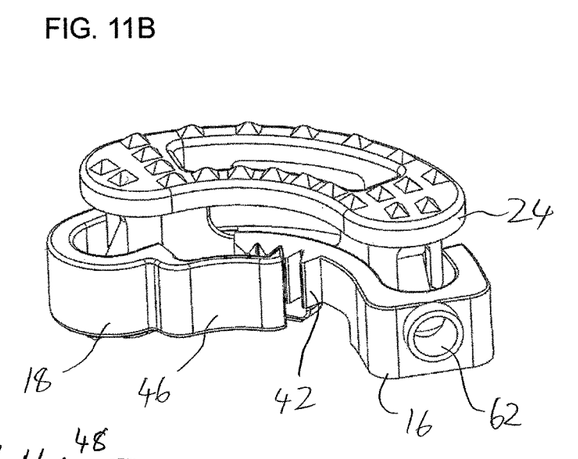

FIGS. 11A-13 illustrate two variant implementations of an implant 10' and 10" which are essentially similar to implant 10 described above, differing only in the form of the ratchet configuration. Specifically, in these variant implementations, the tooth edges of ratchet teeth 42 are aligned substantially perpendicular (i.e., within +/−15 degrees of perpendicular) to a plane containing the arcuate path of relative motion. In the implementation of FIGS. 11A-11C, a ratchet configuration is provided only on the inside of the arcuate form, whereas in the implementation of FIGS. 12A-13, ratchet configurations are provided both on the inside and outside of the arcuate form.

Figure 11C:
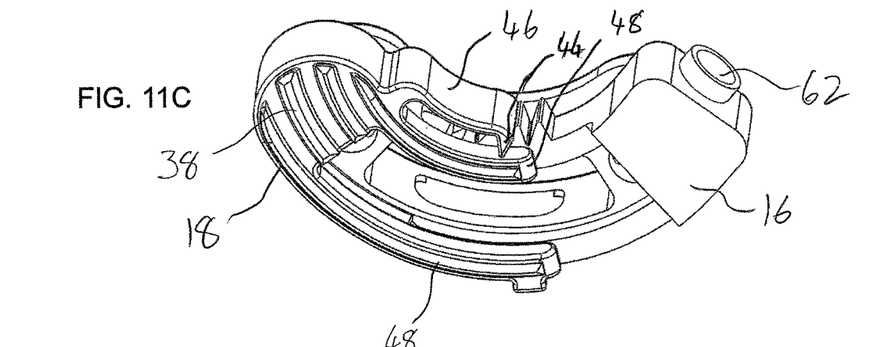
Figure 12A:
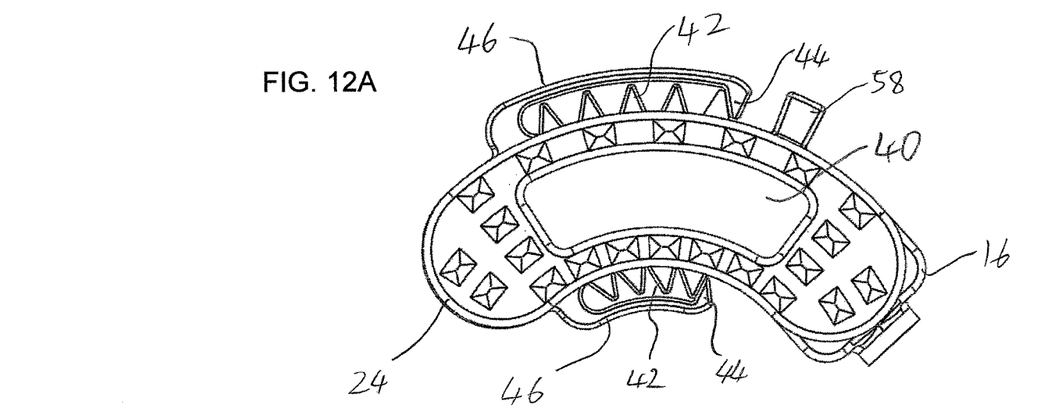
FIGS. 12A and 12B are a plan view and a low isometric view, respectively, of a second variant implementation of an expanding implant, constructed and operative according to an embodiment of the present invention, employing a second alternative implementation of a ratchet configuration.
Figure 12B:
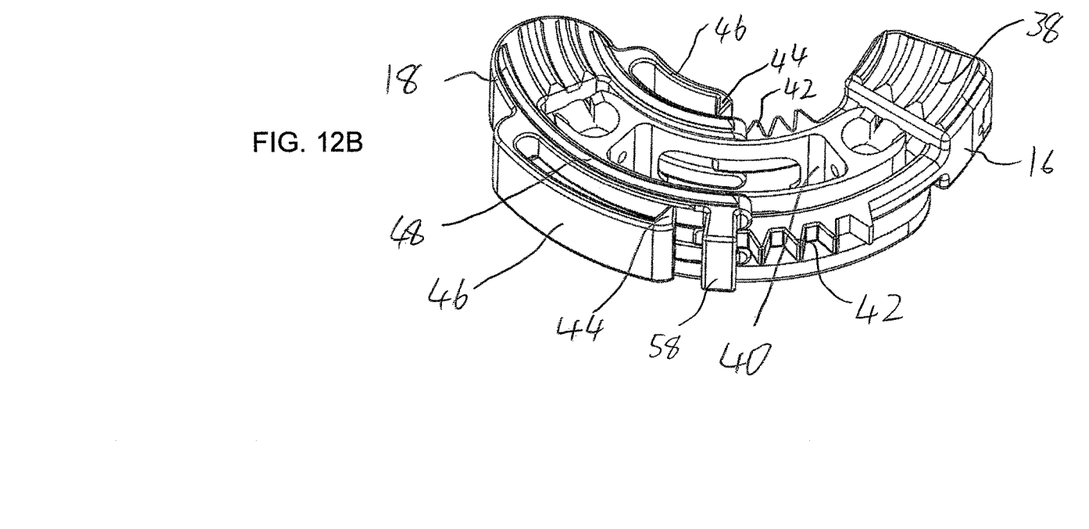
Figure 13:
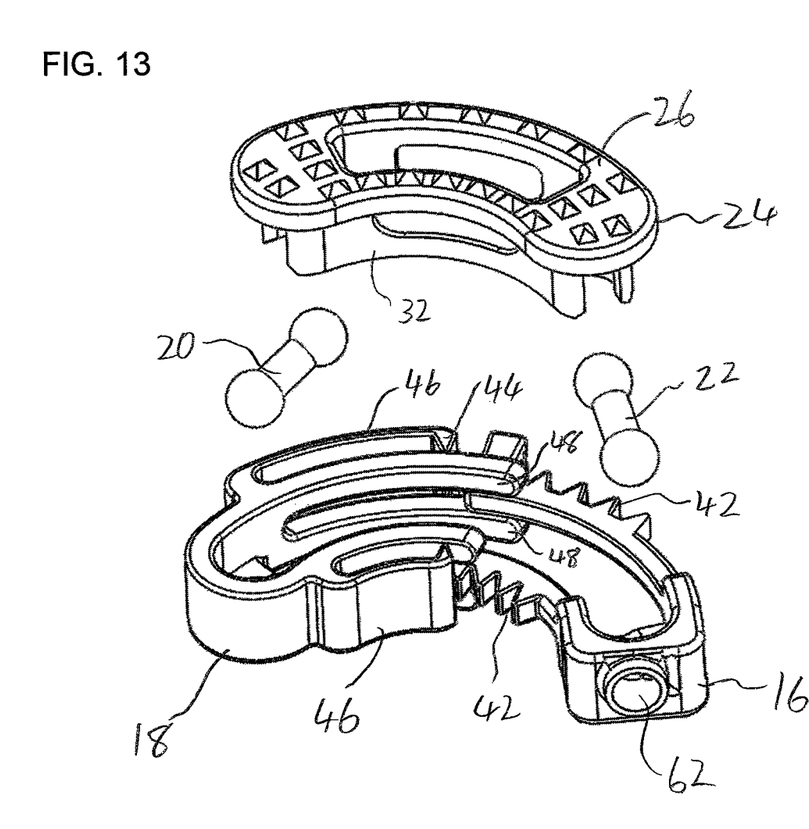
FIG. 13 is an exploded isometric view of the implant of FIG. 12A.

In this implementation, the pawl structure of tooth 44 and resilient arm 46 extends externally to the sequence of ratchet teeth, and the motion of tooth 44 as it passes over the ratchet teeth is within the plane of the arcuate path of relative motion. In order to provide extended arcuate bearing surfaces for distal portion 18, additional arcuate arms 48 preferably extend beneath and/or above series of ratchet teeth 42, as best seen in FIGS. 11C and 13.

Figure 7A:
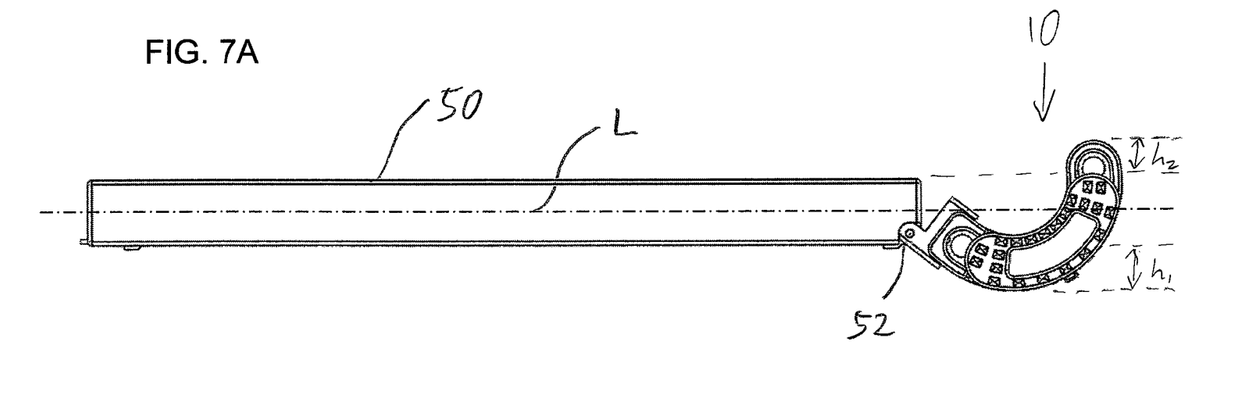
FIGS. 7A and 7B are plan views of the implant-holder combination of FIG. 6A showing the implant in an insertion position and pivoted to a laterally deflected position, respectively.
Figure 7B:
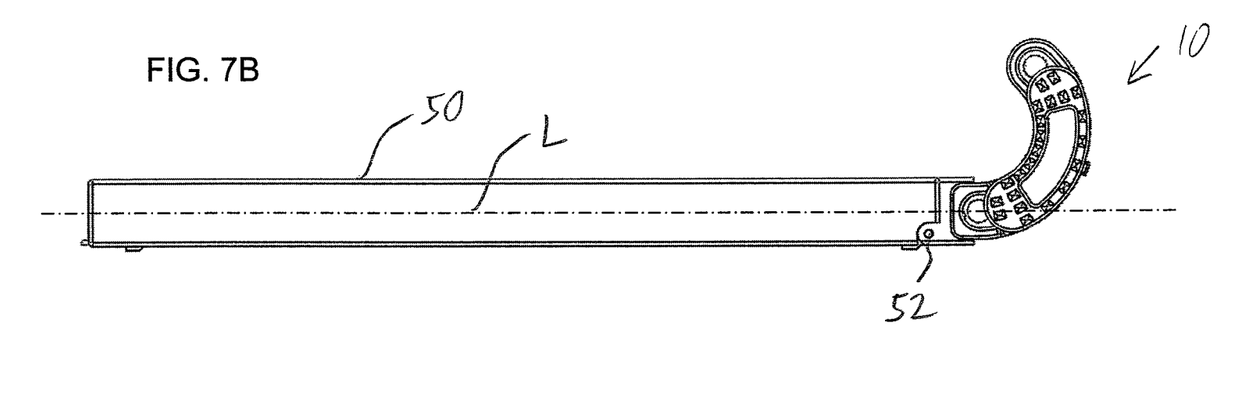
Figure 8A:
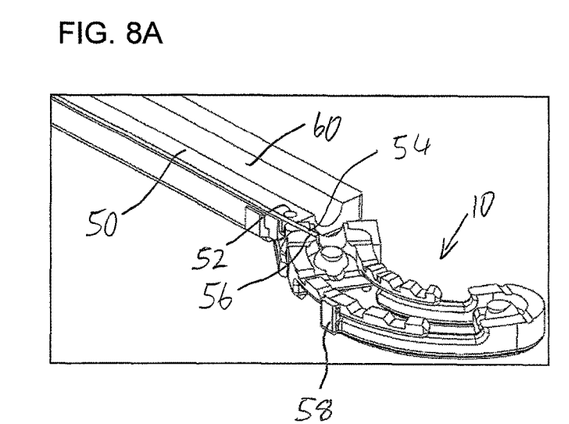
FIGS. 8A-8D are in-plane cut-away isometric views of a distal part of the holder and the implant from FIG. 6A showing the implant locked in the insertion position, unlocked, deflected to a laterally deflected position, and locked in the laterally deflected position, respectively.
Figure 8B:
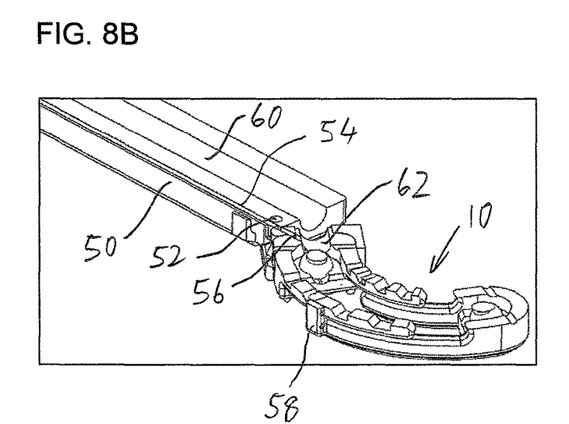
Figure 8C:
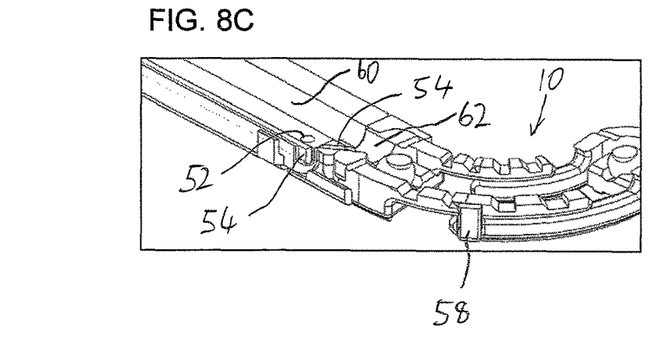
Figure 8D:
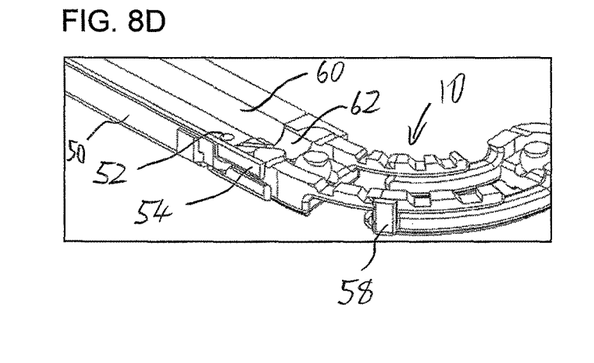
Figures 9A, 9B:
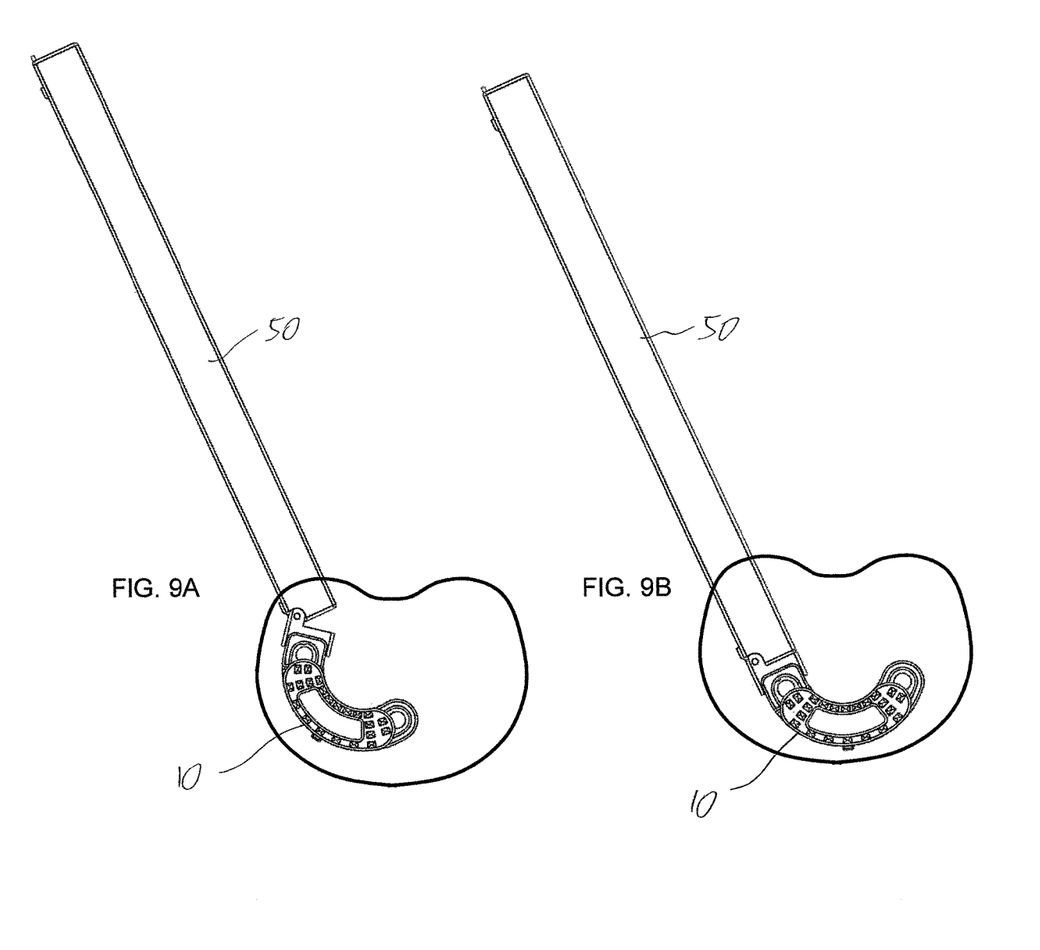
FIGS. 9A and 9B are schematic plan views of a vertebral endplate illustrating two stages in the deployment of the implant of FIG. 1A.
Figure 10:
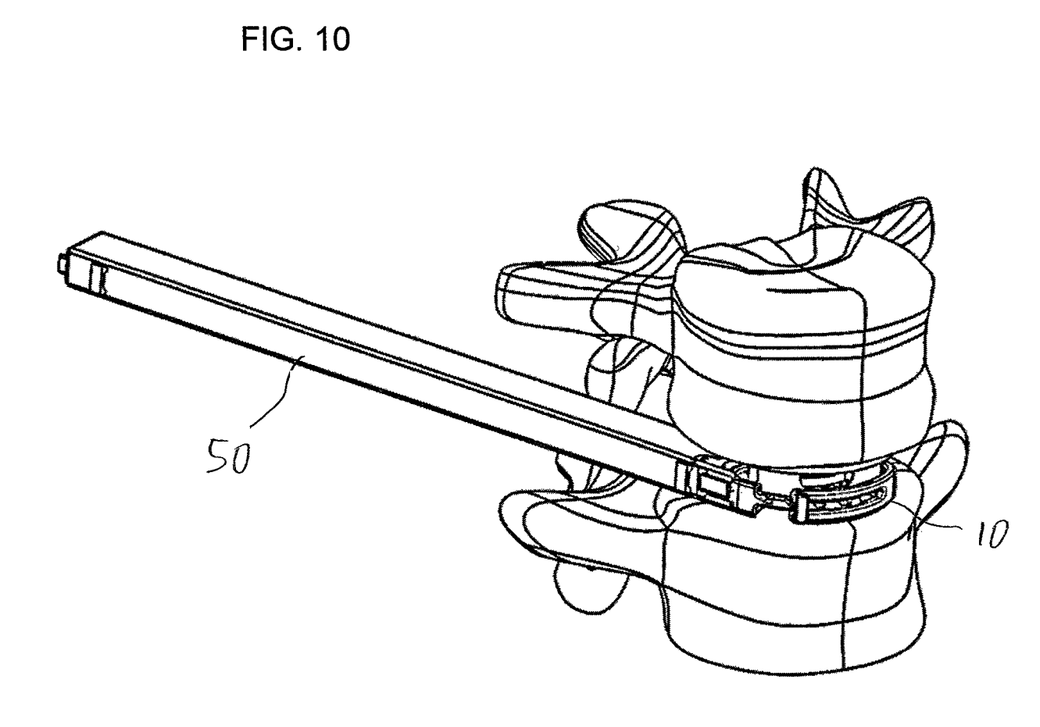
FIG. 10 is a schematic isometric view of the implant of FIG. 1A deployed and expanded in the anterior half of an intervertebral space.

Turning now to FIGS. 6A-10, implant 10 (or 10' or 10") is preferably used as part of a system that includes an elongated holder 50 that has a direction of elongation "L" (FIG. 7A-7B). Implant 10 is pivotally connected to a distal end of elongated holder 50 at a hinge 52 so as to be pivotable about a pivot axis perpendicular to the arcuate path of relative motion between an insertion position (FIGS. 7A, 9A) in which distal portion 18 is aligned with direction of elongation L and a laterally deflected position (FIG. 7B, 9B). In the insertion position, the positioning of the implant relative to the holder is preferably such that the implant is primarily "ahead" of the holder, with relatively small lateral overhangs $h_1$ and $h_2$ beyond the projected width of the holder in both directions (see FIG. 7A). This facilitates insertion of the implant via a small opening, as represented schematically in FIG. 9A. Once within the intervertebral space, by assuming the laterally deflected position, the implant can be brought to a desired position, roughly symmetrically deployed in the anterior half of the intervertebral space, with its curvature fining to the anterior endplate shape, as illustrated in FIGS. 9B and 10. Hinge 52 is implemented as a remotely releasable hinge which can be released by a user holding the proximal end of holder 50 (details of mechanism not shown), to allow the holder to be disconnected from the implant and withdrawn, leaving the implant correctly positioned within the body. Detachable hinge connections are well known in the art, and for conciseness, will not be described here in detail.

In order to prevent premature deflection of implant 10, the system preferably includes a locking element 54 extending along elongated holder 50 for selectively engaging a corresponding recess 56 in proximal portion 16 so as to lock the expanding implant in the insertion position. This engagement is best seen in FIG. 8A. Locking element 54 is selectively retractable, as shown in FIG. 8B, so as to release implant 10 to deflect towards the laterally deflected position (FIG. 8C). Preferably, implant 10 and hinge 52 are further configured to allow advancing of locking element 54 when the implant is in the laterally deflected state so as to retain the implant in that state, either by entering a second complementary recess or by abutting an external surface of the implant, as shown in FIG. 8D.

In order to actuate a change in arcuate extent of the base, and thereby adjust the height of the implant, an actuating element preferably extends along elongated holder 50. In the case illustrated here, where shortening of the base is used to expand the height, actuation is preferably performed by use of a tensioning element (not shown) which extends along elongated holder 50 and is connected to distal portion 18 at a dedicated connector block 58. The tensioning element may be a wire, cable, strip or other tensioning element, formed from metal, polymer or other natural or man-made materials. Tension applied to the tensioning element is effective to shorten the base towards the second state, thereby progressively actuating an increase in height, which is then retained by the ratchet mechanism.

Also visible in FIGS. 8A-8D is an access channel 60 extending along holder 50 which is aligned with a proximal filling port 62 of implant 10. Access channel 60 and filling port 62 together provide an access route to an internal volume of the implant. During deployment, this access route is available for insertion of a tool, if required, for releasing the ratchet engagement and/or otherwise forcing re-extensors of base 12 so as to facilitate repositioning or removal of the implant. After successful deployment, access channel 60 and filling port 62 are typically used for introduction of biocompatible filler materials, such as bone graft or other bone-growth-inducing materials.

At this stage, the operation of the invention, and the corresponding method, will already be clear. After the opening a suitable access opening, typically by a posterior or lateral-posterior approach, and preparing the intervertebral space for the implant, holder 50 is used to introduce implant 10 (or 10' or 10") in the insertion state between two vertebral endplates (FIG. 9A). Locking element 54 is then withdrawn so that, during further advancing of the implant and/or by a supplementary tensioning element (not shown) linked to the inside of the arcuate form, the implant is pivoted to its laterally deflected position and deployed in an anterior half of an intervertebral space (FIGS. 9B and 10). The tensioning element is then actuated to cause relative motion of the base portions so as to increase the height of the implant, thereby pressing contact surfaces 14 and 26 against the two vertebral endplates. At this point, a quantity of bone-promoting material is typically introduced into an inner volume of the implant to promote intervertebral fusion. Holder 50 is then detached from the implant so as to leave the implant as a spacer between the vertebral endplates.

Implant 10 may be formed from any material or combination of materials which are biocompatible and exhibit suitable mechanical properties. Examples include, but are not limited to, titanium and various polymer materials. Although illustrated herein with roughly parallel contact surfaces, it should be noted that the implant can readily be implemented with more rounded edges, one or both of the upper and lower surfaces can be implemented with a convex curvature to more closely an "anatomical contour", and the device may be provided with angled surface which further contribute to restoration of a lordotic angle. Additionally or alternatively, distal portion 18 and/or the distal part of displaceable portion 24 may be shaped to provide a "bullet nose" shape (i.e., tapered and ending in a rounded tip) to facilitate insertion into the intervertebral disc space.

It will be appreciated that the above descriptions are intended only to serve as examples, and that many other embodiments are possible within the scope of the present invention as defined in the appended claims.

What is claimed is:

1. An expanding implant for insertion between two regions of tissue, the implant comprising:
   a base having a contact surface for contacting a first region of tissue, said base comprising a proximal portion in sliding engagement with a distal portion so as to define an arcuate path of relative motion between said proximal portion and said distal portion, said base assuming an initial state with a first arcuate extent and being adjustable towards a second state by changing an extent of overlap to vary an arcuate extent of said base;
   a displaceable portion having a contact surface for contacting a second region of tissue;
   a first rigid linking segment having a first end and an opposing second end, said first end including a first articulating connection with said displaceable portion and said second end including a second articulating connection with said distal portion of said base;
   a second rigid linking segment having a first end and an opposing second end, said first end including a third articulating connection with said displaceable portion and said second end including a fourth articulating connection with said proximal portion of said base;
   wherein each one of said first articulating connection, said second articulating connection, said third articulating connection, and said fourth articulating connection is a polyaxial joint such that adjustment of said base from said initial state towards said second state causes an increase in a distance between said contact surfaces of said base and said displaceable portion.

2. The expanding implant of claim 1, wherein said adjustment of said base from said initial state towards said second state corresponds to a shortening of said base by increasing said extent of overlap between said proximal portion and said distal portion.

3. The expanding implant of claim 1, wherein said polyaxial joints are ball-and-socket joints.

4. The expanding implant of claim 1, wherein said displaceable portion includes at least one arcuate bearing surface extending away from said contact surface, and wherein said proximal portion and said distal portion of said base each include at least one arcuate abutment surface in sliding engagement with said at least one arcuate bearing surface, thereby at least partially defining said arcuate path of relative motion between said proximal portion and said distal portion.

5. The expanding implant of claim 1, wherein said displaceable portion and said base are each formed with openings through their respective said contact surfaces such that said openings provide at least one unobstructed path between the first and the second regions of tissue.

6. The expanding implant of claim 1, wherein said proximal portion and said distal portion of said base are formed with complementary parts of a ratchet configuration configured to allow adjustment of said base towards said second state and to oppose return of said base back towards said initial state.

7. The expanding implant of claim 6, wherein said ratchet configuration includes a first series of ratchet teeth deployed along an inner side of an arcuate form of the implant and a second series of ratchet teeth deployed along an outer side of the arcuate form of the implant, wherein an inter-tooth spacing of said second series of ratchet teeth is greater than an inter-tooth spacing of said first series of ratchet teeth.

8. The expanding implant of claim 6, wherein said ratchet configuration includes a plurality of teeth, each of said teeth having a tooth edge, said ratchet configuration being oriented such that said tooth edges are aligned substantially perpendicular to a plane containing said arcuate path of relative motion.

9. The expanding implant of claim 6, wherein said ratchet configuration includes a plurality of teeth, each of said teeth having a tooth edge, said ratchet configuration being oriented such that said tooth edges are substantially within to a plane containing said arcuate path of relative motion.

10. The expanding implant of claim 1, further comprising an elongated holder having a direction of elongation, the expanding implant being pivotally connected to a distal end of said elongated holder so as to be pivotable about a pivot axis between an insertion position in which said distal portion is aligned with said direction of elongation and a laterally deflected position, said pivot axis being perpendicular to said arcuate path of relative motion.

11. The expanding implant of claim 10, further comprising a locking element extending along said elongated holder for selectively engaging a corresponding recess in said proximal portion so as to lock the expanding implant in said insertion position, said locking element being selectively retractable so as to release the expanding implant to deflect towards said laterally deflected position.

12. The expanding implant of claim 10, further comprising a tensioning element extending along said elongated holder and along said proximal portion, said tensioning element being connected to said distal portion such that tension applied to said tensioning element is effective to shorten said base towards said second state.

13. A method of use of an implant and holder according to claim 10, the method comprising the steps of:
  (a) using said holder to introduce the implant in said insertion state between two vertebral endplates;
  (b) pivoting the implant to said laterally deflected position and deploying the implant in an anterior half of an intervertebral space; and
  (c) causing relative motion of the base portions so as to press the contact surfaces against the two vertebral endplates; and
  (d) detaching the holder from the implant so as to leave the implant as a spacer between the vertebral endplates.

14. The method of claim 13, further comprising introducing a quantity of bone-promoting material into an inner volume of the implant as part of an intervertebral fusion process.

15. An expanding implant for insertion between two regions of tissue, the implant comprising:
  a base having a contact surface for contacting a first region of tissue, said base comprising a proximal portion in sliding engagement with a distal portion so as to define an arcuate path of relative motion between said proximal portion and said distal portion, said base assuming an initial state with a first arcuate extent and being adjustable towards a second state by changing an extent of overlap to vary an arcuate extent of said base;
  a displaceable portion having a contact surface for contacting a second region of tissue;
  a first rigid linking segment having a first polyaxial joint with each one of said distal portion of said base and said displaceable portion;
  a second rigid linking segment having a second polyaxial joint with each one of said proximal portion of said base and said displaceable portion; and
  one or more guide slots within at least one of said displaceable portion and said base limiting the range of motion of said first rigid linking segment and said second rigid linking segment allowed by said first polyaxial joints and said second polyaxial joints such that adjustment of said base from said initial state towards said second state causes an increase in a distance between said contact surfaces of said base and said displaceable portion.

16. The expanding implant of claim 15, wherein said displaceable portion includes said one or more guide slots.

* * * * *